(12) United States Patent
Bevec

(10) Patent No.: US 7,951,778 B2
(45) Date of Patent: *May 31, 2011

(54) USE OF COMPOUNDS HAVING THE BIOLOGICAL ACTIVITY OF VASOACTIVE INTESTINAL PEPTIDE FOR THE TREATMENT OF SARCOIDOSIS

(75) Inventor: Dorian Bevec, Gentilino (CH)

(73) Assignee: mondoBIOTECH AG (CH)

( * ) Notice: Subject to any disclaimer, the term of this patent is extended or adjusted under 35 U.S.C. 154(b) by 323 days.

This patent is subject to a terminal disclaimer.

(21) Appl. No.: 11/804,780

(22) Filed: May 21, 2007

(65) Prior Publication Data

US 2008/0274961 A1 Nov. 6, 2008

Related U.S. Application Data

(62) Division of application No. 10/517,125, filed as application No. PCT/CH03/00357 on Jun. 5, 2003, now abandoned.

(30) Foreign Application Priority Data

Jun. 10, 2002 (EP) ..................................... 02012767

(51) Int. Cl.
*A61K 38/00* (2006.01)
*A61K 38/16* (2006.01)
(52) U.S. Cl. .......................... 514/13.1; 514/1.1; 424/9.2
(58) Field of Classification Search ........................ None
See application file for complete search history.

(56) References Cited

U.S. PATENT DOCUMENTS

| | | | |
|---|---|---|---|
| 3,880,826 | A | 4/1975 | Said et al. |
| 3,898,329 | A | 8/1975 | Said et al. |
| 4,179,337 | A | 12/1979 | Davis et al. |
| 4,237,046 | A | 12/1980 | Bodanszky |

FOREIGN PATENT DOCUMENTS

| | | |
|---|---|---|
| EP | 0184309 | 6/1986 |
| EP | 0225020 | 6/1987 |
| EP | 0325044 | 7/1989 |
| EP | 0204447 | 10/1991 |
| EP | 0405242 | 10/1991 |
| EP | 0463450 | 2/1994 |
| EP | 0613904 | 9/1994 |
| EP | 0620008 | 9/1994 |
| EP | 0536741 | 4/1995 |
| EP | 0663406 | 7/1995 |
| EP | 0401384 | 3/1996 |
| WO | WO-8905857 | 6/1989 |
| WO | WO-9106565 | 1/1995 |
| WO | WO-9527496 | 10/1995 |
| WO | WO-9729126 | 8/1997 |
| WO | WO-9735561 | 10/1997 |
| WO | WO-01/34088 | 5/2001 |
| WO | WO-0116295 | 8/2001 |
| WO | WO 02/43746 | * 6/2002 |
| WO | WO-0243746 | 6/2002 |

OTHER PUBLICATIONS

Rudinger J, "Characteristics of the amino acids as components of a peptide hormone sequence," Peptide Hormones, Edited by JA Parsons, University Park Press, Jun. 1976, pp. 1-7.*
"Designing Custom Peptides" from SIGMA Genosys, pp. 1-2. Accessed Dec. 16, 2004.*
Schinzel R, Drueckes P, "The phosphate recognition site of Escherichia coli maltodextrin phosphorylase," FEBS, Jul. 1991, 286(1,2): 125-128.*
Berendsen HJC, "A Glimpse of the Holy Grail?" Science, Oct. 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Sarcoidosis from Merck manual, pp. 1-6. Accessed Sep. 21, 2009.*
Francis, Gillian E., "Protein modification and fusion proteins", Focus on Growth Factors, vol. 3, No. 2, May 1992, (pp. 4-10).
Remington's Pharmaceutical Sciences 18th edition (1990), Mack Publishing Company, Chapter 75, Alfonso R. Gennaro, Editor and Chairman, (pp. 1435-1450).
Remington's Pharmaceutical Sciences 18th edition (1990), Mack Publishing Company, Chapter 83, Alfonso R. Gennaro, Editor and Chairman, (pp. 1519-1544).
Remington's Pharmaceutical Sciences 18th edition (1990), Mack Publishing Company, Chapter 88, Alfonso R. Gennaro, Editor and Chairman, (pp. 1615-1632).

(Continued)

Primary Examiner — Julie Ha
(74) Attorney, Agent, or Firm — Winstead PC

(57) ABSTRACT

The present invention relates to peptides which are highly biologically and pharmacologically active as therapeutic drug for the treatment of diseases related to sarcoidosis. The peptides which can be used according to the invention for the treatment of said disease comprise at least one specific highly conservative amino acid residue sequence which seem to play an important role in connection with pulmonary and arteriolar hypertension events. It could be shown that the known naturally occurring peptides "vasoactive intestinal peptide (VIP)" and "pituitary adenylate cyclase-activating polypeptide (PACAP)", having these specific sequences are potent drugs which can be successfully used for treatment of sarcoidosis. Furthermore, the present invention discloses a method for the treatment patients suffering from sarcoidosis.

5 Claims, No Drawings

OTHER PUBLICATIONS

Remington's Pharmaceutical Sciences 18th edition (1990), Mack Publishing Company, Chapter 89, Alfonso R. Gennaro, Editor and Chairman, (pp. 1633-1665).

Remington's Pharmaceutical Sciences 18th edition (1990), Mack Publishing Company, Chapter 92, Alfonso R. Gennaro, Editor and Chairman, (pp. 1694-1712).

Keith I.M. Physiological Research, vol. 49(5), 2000, pp. 519-537 "The role of endogenous lung neuropeptides in regulation of the pulmonary circulation".

Pavlou T. A. et al., "Infusion of Vasoactive Intestinal Peptide Improves Hemodynamics in Primary Pulmonary Hypertension", American Review of Respiratory Disease, vol. 14, 1993, p. A536 Suppl. S.

Iwanga et al., "Vasoactive Intestinal Peptide VIP Protects Against Acid-Induced Acute Lung Injury in Isolated Perfused Rat Lungs," 1989 Japanese Journal of Thoracic Diseases vol. 27(7) pp. 789-795 (Abstract only).

Maruno et al., "VIP inhibits basal and histamine-stimulated proliferation of human airway smooth muscle cells," 1995 American Journal of Physiology vol. 268(6) pp. L1047-L1051.

Kawasaki et al., "The mechanisms of the relaxation induced by vasoactive intestinal peptide in the porcine coronary artery," 1997 British Journal of Pharmacology Vo. 121(5) pp. 977-985.

Platoshyn et al., "Sustained membrane depolarization and pulmonary artery smooth muscle cell proliferation" Nov. 1, 2000 American Journal of Physiology vol. 279(5) pp. C1540-C1549.

Hultgardh et al.; "Growth-inhibitory properties of vasoactive intestinal polypeptides."; Regul. Pept.; p. 267-274; 1998.

Ishihara et al.; "Functional expression and tissue distribution of a novel receptor for vasoactive intestinal polypeptide."; Nueron 8; p. 811-819; 1992.

Mood et al.; Proceedings of the National Academy of Science, USA, 90; p. 4345; 1992.

Wollman et al.; Brain Research 624; p. 339; 1993.

Said, S. I.; "Vasoactive intestinal polypeptide (VIP) in asthma."; Annals New York Academy of Science, 629; p. 305-318; 1991.

Hamasaki et al.; "Relaxant action of VIP on cat pulmonary artery: comparison with acetylcoholine, isoproterenol, and PGE1."; Journal of Applied Physiology, 54; p. 1607-1611; 1982.

Iwabuchi et al.; "Vasoactive intestinal peptide causes nitric oxide-dependent pulmonary vasodilation in isolated rat lung."; Respiration, 64; p. 54-58; 1997.

Saga et al.; "Vasoactive intestinal peptide relaxes strips of human bronchus, pulmonary artery, and lung parenchyma."; Trans Association of American Physicians, 97; p. 304-310; 1984.

Raderer et al. "1231-labelled vasoactive intestinal peptide receptor scintigraphy in patients with colorectal cancer."; British Journal of Cancer, 78; p. 1-5; 1998.

Raderer et al.; "Iodine-123-vasoactive intestinal receptor scanning in patients with pancreatic cancer."; Journal of Nuclear Medicine, 39; p. 1570-1575; 1998.

Raderer et al.; "Value of peptide receptor scintigraphy using (123)I-vasoactive intestinal peptide and (111) In-DTPA-D-Phel-octreotide in 194 carcinoid patients."; Vienna University Experience 1993-1998; Journal of Clinical Oncology, 18; p. 1331-1336; 2000.

Virgolini et al.; "Vasoactive intestinal peptide receptor scintography."; Journal of Nuclear Medicine, 36; p. 1732-1739; 1995.

Sada et al.; Journal of Fermentation Bioengineering, 71; p. 137-139; 1999.

Newman et al.; "Sacroidosis"; New England Journal of Medicine, 336; p. 1224-1234; 1997.

Chesnutt, A. N.; "Enigmas in Sarcoidosis"; Western Journal of Medicine, 162; p. 519-526; 1995.

Rakel, R. E.; "Conn's current thearapy 1995: latest approved methods of treatment for the practicing physician."; Philadelphia: Saunders 1995; p. 195-199.

Crystal et al.; "Interstitial lung diseases of unkown cause. Disorders characterized by chronic inflamation of the lower respiratory tract (first of two parts)"; New England Journal of Medicine, 310; p. 154-166; 1984.

Staton et al.; "Chronic diffuse infiltrative lung disease"; Scientific American; p. 11-24; 1997.

Winterbauer et al.; "Use of pulmonary function tests in the management of sarcoidosis."; Chest Journal, 78; p. 640-647; 1980.

Muther et al.; "Renal manifestations of sarcoidosis."; Archive of Internal Medicine, 141; p. 643-645; 1981.

DeRemee; "Sarcoidosis"; Mayo Clinic Proceedings, 70; p. 177-181; 1995.

Sharma et al.; "Myocardial Sarcoidosis"; Chest Journal, 103; p. 253-258; 1993.

Eklund; "Sarcoidosis. Conn's current therapy 1997: latest approved methods of treatment for practicing physicians."; Philidelphia: Saunders; p. 229-231; 1997.

"Remedy for dermal ulcer—comprises vasoactive intestinal polypeptide as active component"; Derwent, XP002249383, 1996.

Dey et al., "Localization of VIP-immunoreactive nerves in airways and pulmonary vessels of dogs, cats, and human subjects." Veterans Administration Medical Center, Dallas, Texas. Cell Tissue Res (1982) 220:231-238.

Abuchowski et al., "Soluble Polymer-Enzyme Adducts." Rutgers University, New Brunswick, New Jersey. 1981, p. 367-383.

* cited by examiner

SEQUENCE LISTING

<160> NUMBER OF SEQ ID NOS: 15

<210> SEQ ID NO 1
<211> LENGTH: 28
<212> TYPE: PRT

<213> ORGANISM: homo sapiens

<400> SEQUENCE: 1

```
His Ser Asp Ala Val Phe Thr Asp Asn Tyr Thr Arg Leu Arg Lys Gln
1               5                   10                  15
Met Ala Val Lys Lys Tyr Leu Asn Ser Ile Leu Asn
            20                  25
```

<210> SEQ ID NO 2
<211> LENGTH: 38
<212> TYPE: PRT
<213> ORGANISM: homo sapiens

<400> SEQUENCE: 2

```
His Ser Asp Gly Ile Phe Thr Asp Ser Tyr Ser Arg Tyr Arg Lys Gln
1               5                   10                  15
Met Ala Val Lys Lys Tyr Leu Ala Ala Val Leu Gly Lys Arg Tyr Lys
            20                  25                  30
Gln Arg Val Lys Asn Lys
            35
```

<210> SEQ ID NO 3
<211> LENGTH: 27
<212> TYPE: PRT
<213> ORGANISM: homo sapiens

<400> SEQUENCE: 3

```
His Ser Asp Gly Ile Phe Thr Asp Ser Tyr Ser Arg Tyr Arg Lys Gln
1               5                   10                  15
Met Ala Val Lys Lys Tyr Leu Ala Ala Val Leu
            20                  25
```

<210> SEQ ID NO 4
<211> LENGTH: 10
<212> TYPE: PRT
<213> ORGANISM: homo sapiens

<400> SEQUENCE: 4

```
Arg Lys Gln Met Ala Val Lys Lys Tyr Leu
1               5                   10
```

<210> SEQ ID NO 5
<211> LENGTH: 23
<212> TYPE: PRT
<213> ORGANISM: homo sapiens
<220> FEATURE:
<221> NAME/KEY: x
<222> LOCATION: (4)..(8)
<223> OTHER INFORMATION: x is any naturally occuring amino acid residue

<400> SEQUENCE: 5

```
Phe Thr Asp Xaa Xaa Xaa Xaa Xaa Arg Lys Gln Met Ala Val Lys Lys
1               5                   10                  15
Tyr Leu Asn Ser Ile Leu Asn
            20
```

<210> SEQ ID NO 6
<211> LENGTH: 23
<212> TYPE: PRT
<213> ORGANISM: homo sapiens

<400> SEQUENCE: 6

```
Phe Thr Asp Asn Tyr Thr Arg Leu Arg Lys Gln Met Ala Val Lys Lys
1               5                   10                  15
```

```
Tyr Leu Asn Ser Ile Leu Asn
            20

<210> SEQ ID NO 7
<211> LENGTH: 18
<212> TYPE: PRT
<213> ORGANISM: homo sapiens

<400> SEQUENCE: 7

Phe Thr Asp Ser Tyr Ser Arg Tyr Arg Lys Gln Met Ala Val Lys Lys
1               5                   10                  15

Tyr Leu

<210> SEQ ID NO 8
<211> LENGTH: 23
<212> TYPE: PRT
<213> ORGANISM: homo sapiens
<220> FEATURE:
<221> NAME/KEY: x
<222> LOCATION: (4)..(5)
<223> OTHER INFORMATION: x is any naturally occuring amino acid residue
<220> FEATURE:
<221> NAME/KEY: x
<222> LOCATION: (9)..(13)
<223> OTHER INFORMATION: x is any naturally occuring amino acid residue

<400> SEQUENCE: 8

His Ser Asp Xaa Xaa Phe Thr Asp Xaa Xaa Xaa Xaa Xaa Arg Lys Gln
1               5                   10                  15

Met Ala Val Lys Lys Tyr Leu
            20

<210> SEQ ID NO 9
<211> LENGTH: 23
<212> TYPE: PRT
<213> ORGANISM: homo sapiens

<400> SEQUENCE: 9

His Ser Asp Ala Val Phe Thr Asp Asn Tyr Thr Arg Leu Arg Lys Gln
1               5                   10                  15

Met Ala Val Lys Lys Tyr Leu
            20

<210> SEQ ID NO 10
<211> LENGTH: 23
<212> TYPE: PRT
<213> ORGANISM: homo sapiens

<400> SEQUENCE: 10

His Ser Asp Gly Ile Phe Thr Asp Ser Tyr Ser Arg Tyr Arg Lys Gln
1               5                   10                  15

Met Ala Val Lys Lys Tyr Leu
            20

<210> SEQ ID NO 11
<211> LENGTH: 28
<212> TYPE: PRT
<213> ORGANISM: homo sapiens
<220> FEATURE:
<221> NAME/KEY: x
<222> LOCATION: (4)..(5)
<223> OTHER INFORMATION: x is any naturally occuring amino acid residue
<220> FEATURE:
<221> NAME/KEY: x
<222> LOCATION: (9)..(13)
<223> OTHER INFORMATION: x is any naturally occuring amino acid residue
```

```
<220> FEATURE:
<221> NAME/KEY: x
<222> LOCATION: (24)..(28)
<223> OTHER INFORMATION: x is any naturally occuring amino acid residue
<220> FEATURE:
<221> NAME/KEY: x
<222> LOCATION: (24)..(28)
<223> OTHER INFORMATION: x is any naturally occuring amino acid residue
      at 24-27; x at position 28 may be H or any naturally occuring
      amino acid residue

<400> SEQUENCE: 11

His Ser Asp Xaa Xaa Phe Thr Asp Xaa Xaa Xaa Xaa Xaa Arg Lys Gln
1               5                   10                  15

Met Ala Val Lys Lys Tyr Leu Xaa Xaa Xaa Xaa Xaa
            20                  25

<210> SEQ ID NO 12
<211> LENGTH: 38
<212> TYPE: PRT
<213> ORGANISM: homo sapiens
<220> FEATURE:
<221> NAME/KEY: x
<222> LOCATION: (4)..(5)
<223> OTHER INFORMATION: x is any naturally occuring amino acid residue
<220> FEATURE:
<221> NAME/KEY: x
<222> LOCATION: (9)..(13)
<223> OTHER INFORMATION: x is any naturally occuring amino acid residue
<220> FEATURE:
<221> NAME/KEY: x
<222> LOCATION: (24)..(38)
<223> OTHER INFORMATION: x is any naturally occuring amino acid residue

<400> SEQUENCE: 12

His Ser Asp Xaa Xaa Phe Thr Asp Xaa Xaa Xaa Xaa Xaa Arg Lys Gln
1               5                   10                  15

Met Ala Val Lys Lys Tyr Leu Xaa Xaa Xaa Xaa Xaa Xaa Xaa Xaa
            20                  25                  30

Xaa Xaa Xaa Xaa Xaa Xaa
            35

<210> SEQ ID NO 13
<211> LENGTH: 3
<212> TYPE: PRT
<213> ORGANISM: homo sapiens

<400> SEQUENCE: 13

Phe Thr Asp
1

<210> SEQ ID NO 14
<211> LENGTH: 3
<212> TYPE: PRT
<213> ORGANISM: homo sapiens

<400> SEQUENCE: 14

His Ser Asp
1

<210> SEQ ID NO 15
<211> LENGTH: 12
<212> TYPE: PRT
<213> ORGANISM: homo sapiens
<220> FEATURE:
<221> NAME/KEY: x
<222> LOCATION: (1)..(1)
<223> OTHER INFORMATION: x is a string of 0 to 25 naturally occuring
      amino acid residues
```

```
<220> FEATURE:
<221> NAME/KEY: x
<222> LOCATION: (12)..(12)
<223> OTHER INFORMATION: x is a string of 0 to 25 naturally occuring
      amino acid residues

<400> SEQUENCE: 15

Xaa Arg Lys Gln Met Ala Val Lys Lys Tyr Leu Xaa
1               5                   10
```

USE OF COMPOUNDS HAVING THE BIOLOGICAL ACTIVITY OF VASOACTIVE INTESTINAL PEPTIDE FOR THE TREATMENT OF SARCOIDOSIS

This patent application is a divisional of U.S. patent application Ser. No. 10/517,125, filed on Aug. 30, 2005 now abandoned as a national stage filing of PCT/CH03/00357, filed on Jun. 5, 2003. U.S. patent application Ser. No. 10/517,125 and International Application No. PCT/CH03/00357 are incorporated herein by reference.

FIELD OF THE INVENTION

The present invention relates to peptides which are highly biologically and pharmacologically active as therapeutic drug for the treatment of pulmonary sarcoidosis. The peptides which can be used according to the invention for the treatment of said disease comprise at least one specific highly conservative amino acid residue sequence which seems to play an important role in connection with biological events underlying the disease. It could be shown that especially the known naturally occurring peptides "vasoactive intestinal peptide (VIP)" and "pituitary adenylate cyclase-activating polypeptide (PACAP)", having these specific sequences are potent drugs which can be successfully used for treatment of sarcoidosis. Furthermore, the present invention discloses pharmaceutical compositions useful for treatment of sarcoidosis within said methods.

BACKGROUND OF THE INVENTION

Sarcoidosis of the lung is primarily an interstitial lung disease in which the inflammatory process involves the alveoli, small bronchi, and small blood vessels. These individuals typically have dyspnea, particularly with exercise and dry cough. Hemoptysis is rare, as is production of sputum.

As sarcoidosis progresses, small lumps, or granulomas, appear in the affected tissues. In the few cases where the granulomas do not heal and disappear, the tissues tend to remain inflamed and become scarred (fibrotic).

From 20 to 30 percent of sarcoidosis patients are left with permanent lung damage. In 10 to 15 percent of the patients, sarcoidosis can become chronic.

Symptoms of sarcoidosis may be caused by a number of factors, including the "mass effect" of the granuloma(s); immune complex vasculitis (as occurs in erythema nodosum); metabolically active granulomas; and fibrotic distortion lasting even after resolution of the granulomatous lesions.

The lungs are the primary target of this disease. About 88 percent of patients with sarcoidosis have lung involvement. It is customary to stage intrathoracic sarcoidosis by comparing current chest radiographs with the chest radiograph taken on initial presentation. Intrathoracic sarcoidosis is divided into four stages. Approximately 8 percent of patients with sarcoidosis present at stage zero. During this stage, the chest radiograph is normal in the presence of multisystem involvement. Results of pulmonary function testing are usually normal, and most patients remit spontaneously. About 51 percent of patients (including the patient described in the illustrative case) present at stage 1. During this stage, chest radiographs show bilateral hilar lymphadenopathy with or without enlarged right paratracheal nodes.

Results of pulmonary function tests are usually normal except for a decreased diffusing capacity, but mechanics are normal. Most patients are asymptomatic or have nonpulmonary symptoms. Most patients (70 to 75 percent) remit within two years, and only 10 to 15 percent progress to stage 2.

Twenty-nine percent of patients with sarcoidosis present at stage 2. During this stage, chest radiographs show hilar lymphadenopathy associated with diffuse pulmonary infiltration. The signs and symptoms are usually mild in relation to the severity of the abnormalities shown on radiograph. Multiple pulmonary nodules or infiltrates may also be present. Results of pulmonary function testing demonstrate restrictive disease with a decreased diffusing capacity, although obstructive changes resulting from bronchial involvement may also be present. One half of these patients undergo spontaneous remission, but 25 to 30 percent remain at stage 2 or progress to stage 3. In patients with stage 3 sarcoidosis, the chest radiograph shows diffuse pulmonary infiltration without hilar lymphadenopathy.

Only about 12 percent of patients present at stage 3. The chest radiograph frequently shows fibrosis with small lung volumes, elevation of the diaphragms and "honeycombing" (fine fibrosis occurring throughout the interstitial lung tissue).

The patient presenting with stage 3 sarcoidosis may have minimal symptoms, (i.e., cough, dyspnea, mild weight loss) or significant problems, including pulmonary hypertension, cor pulmonale and respiratory failure. Many patients in stage 3 have intrinsic restrictive changes on pulmonary function testing but, as a result of bronchial involvement, many also have obstructive changes. Patients at stage 3 usually undergo a chronic course; complications such as pulmonary fibrosis are common and irreversible. Also, at this stage, extrapulmonary findings are more common, especially skin involvement.[6] In up to 30 percent of patients at stage 3, sarcoidosis spontaneously remits within two years.

Table 1 shows the stages of sarcoidosis and the radiographic findings at the time of diagnosis. Other intrathoracic radiographic findings seen in patients with sarcoidosis include alveolar infiltrates that may appear extensive or patchy, atelectasis, nodular cavitation, pleural thickening, pleural effusions and calcifications.

TABLE 1

Stages of Sarcoidosis

Stage
Patients presenting at this stage (%)
Findings on chest radiograph
Results of pulmonary function testing
Signs and symptoms
Patients expected to go into remission (%)

0
8 to 10
Normal (but with multisystem involvement)
Normal
Varies with system affected
Most remit spontaneously
1
51
Bilateral hilar lymphadenopathy with or without enlarged right paratracheal nodes
Normal, except for decreased diffusing capacity; normal mechanics
Most asymptomatic or with nonpulmonary complaints
70 to 75% remit within two years; 10 to 15% progress to stage 2
2
29
Hilar lymphadenopathy with diffuse pulmonary infiltration; pulmonary nodules may be seen
Usually restrictive changes with decreased diffusing capacity; obstructive changes may bepresent

TABLE 1-continued

Stages of Sarcoidosis

Stage
Patients presenting at this stage (%)
Findings on chest radiograph
Results of pulmonary function testing
Signs and symptoms
Patients expected to go into remission (%)

Usually mild in relation to the severity of the radiographic findings
50% spontaneously remit; 25 to 30% persist at stage 2 or progress to stage 3
3
12
Diffuse pulmonary infiltration, but without hilar lymphadenopathy; fibrosis; small lung volumes; elevated diaphragms; effusions; calcifications; "honeycombing"
Primarily restrictive changes, but with obstructive changes due to bronchial involvement; changes may be severe
Varies: may be minimal (cough, dyspnea, weight loss) to severe (cor pulmonale, pulmonary hypertension; may progress to respiratory failure)
30% spontaneously remit within two years Information from reference. Chesnutt AN. Enigmas in sarcoidosis. West J Med 1995; 162: 519-26.

The goals of treatment for sarcoidosis include resolving inflammatory lesions that are interfering with organ function, preventing pulmonary fibrosis and diminishing symptoms. If the patient presents with stage 1 or stage 2 disease with normal pulmonary function tests and no life-threatening signs or symptoms, observation is all that is necessary, as sarcoidosis is usually a self-limited disease and does not require specific therapy. Treatment is indicated if the patient has systemic symptoms or if deterioration in lung function is present at any stage, or if the patient presents with or progresses to stage 3 disease.

Corticosteroids continue to be the mainstay of therapy, although they have not been proved to prolong life. Several different protocols exist. To induce disease regression, treatment with prednisone may be started at a dosage of 40 to 60 mg per day given in divided doses for six to eight weeks, then tapered to a dosage of 15 to 20 mg per day over four to six months. A dosage of 40 to 60 mg of prednisone every other day has also been used for initial treatment, with excellent results.[3,8]

A patient may then be maintained on a dosage of 5 to 10 mg per day to suppress disease activity for up to one year. Patients should receive treatment if they have the following forms of sarcoidosis: hypercalcemia and hypercalciuria, disfiguring skin lesions, ocular sarcoidosis (this should be treated with topical and/or systemic steroids), cardiac sarcoidosis, neurologic sarcoidosis and other organ involvement that is determined to be clinically severe.[8] Relapse occurs in 25 to 40 percent of patients with sarcoidosis within two to three months after discontinuing corticosteroid therapy. If this occurs, clinical examination and laboratory testing should be repeated. Some experts utilize "pulse therapy" with intravenous methylprednisolone at a dosage of 3 g per day for three days during acute exacerbations.[3] Inhaled steroids have been used in patients with sarcoidosis for relief of symptoms, but it has not been proved that this therapy reduces disease progression. Inhaled and oral bronchodilators, supplemental oxygen and synthetic "liquid" tears have also been used to reduce symptoms. Topical ophthalmic steroids have been used to reduce ocular manifestations of sarcoidosis. If symptoms of erythema nodosum and arthritis are present in patients with stage 2 disease, a nonsteroidal anti-inflammatory drug such as indomethacin (Indocin), in a dosage of 25 mg three times daily, may be used.[8]

Newer therapies have been reported. Hydroxychloroquine (Plaquenil), given in a dosage of 200 mg every other day for nine months, may be useful in the treatment of cutaneous sarcoidosis but can permanently damage the eyes; consequently, ocular examinations must be performed frequently. Hydroxychloroquine has also been found to be helpful in the management of hypercalcemia.[1] Methotrexate (Rheumatrex), in a low dosage of 7.5 to 15 mg once per week, has been shown to be of benefit in the treatment of refractory sarcoidosis, especially musculoskeletal and cutaneous forms.[1] Other treatments are available, but few controlled trials have been performed: chlorambucil (Leukeran), cyclophosphamide (Cytoxan) and azathioprine (Imuran). Rarely, lung transplantation has been performed in patients with severe, refractory disease, with varying results. Several patients had a recurrence of granulomatous disease in the transplanted lung.[2,10]

Vasoactive Intestinal Peptide (VIP):

VIP is a 28 amino acid peptide consisting of the following amino acid sequence (from N- to C-terminal):

```
                                          (SEQ ID No. 1)
His-Ser-Asp-Ala-Val-Phe-Thr-Asp-Asn-Tyr-Thr-Arg-

Leu-Arg-Lys-Gln-Met-Ala-Val-Lys-Lys-Tyr-Leu-Asn-

Ser-Ile-Leu-Asn.
```

Healthy individuals exhibit low concentration of VIP (<40 pg/ml serum).

VIP is a widely distributed peptide hormone which mediates a variety of physiological responses including gastrointestinal secretion, relaxation of gastrointestinal vascular and respiratory smooth muscle, lipolysis in adipocytes, pituitary hormone secretion, and excitation and hyperthermia after injection into the central nervous system. Under physiologic conditions VIP acts as a neuroendocrine mediator. Some recent findings suggest that VIP also regulates growth and proliferation of normal as well as malignant cells (Hultgardh, Nilsson A., Nilsson, J., Jonzon, B. et al. *Growth-inhibitory properties of vasoactive intestinal polypeptide. Regul. Pept.* 22, 267-274. 1988). The biological effects are mediated via specific receptors (VIP-R) located on the surface membrane of various cells (Ishihara, T., Shigemoto, R., Mori, K. et al. *Functional expression and tissue distribution of a novel receptor for vasoactive intestinal polypeptide. Neuron* 8, 811-819. 1992). VIP may exert stimulating and trophic effects on neoplastic cells from neuroblastoma, breast, lung and colon cancer (e.g. Moody et al., *Proc. Natl. Acad. Sci. USA,* 90, 4345, 1993), inducing its own receptors by feedback mechanisms. In some cases VIP produced dose-dependent stimulation of mitosis (Wollman et al., *Brain Res.,* 624, 339, 1993). VIP and biologically functional analogues and derivatives thereof are shown to have vascular smooth muscle relaxant activity (Maruno, K, Absood, A., and Said, S. I. *VIP inhibits basal and histamine-stimulated proliferation of human airway smooth muscle cells. Am. J. Physiol.* 268, L1047-L1051, 1995), hair growth activity, apoptosis activity enhanced sustained bronchodilation activity without remarkable cardiovascular side effects, and are effective at disorders or diseases relating to bronchial spasms including asthma, some cases of hypertension, impotence, ischaemia, dry eye and mental disorders, such as Alzheimer's disease (see e.g. WO 9106565, EP 0536741, U.S. Pat. No. 3,880,826, EP 0204447, EP 0405242, WO 9527496, EP 0463450, EP 0613904, EP 0663406, WO 9735561, EP 0620008).

VIP receptor has been detected on airway epithelium of the trachea and the bronchioles. It is also expressed in macrophages surrounding capillaries, in connective tissue of trachea and bronchi, in alveolar walls, and in the subintima of pulmonary veins and pulmonary arteries. Pepidergic nerve fibers are considered the source of VIP in the lungs (e.g.: Dey, R. D., Shannon-W A, Jr, and Said, S. I. *Localization of VIP-immunoreactive nerves in airways and pulmonary vessels of dogs, cat, and human subjects. Cell and Tissue Research* 220, 231-238. 1981; Said, S. I. *Vasoactive intestinal polypeptide (VIP) in asthma. Ann. N.Y. Acad. Sci.* 629, 305-318. 1991). VIP decreases the resistance in the pulmonary vascular system (e.g.: Hamasaki, Y., Mojarad, M., and Said, S. I. *Relaxant action of VIP on cat pulmonary artery: comparison with acetylcholine, isoproterenol, and PGE1. J. Appl. Physiol.* 54, 1607-1611. 1983; Iwabuchi, S., Ono, S., Tanita, T. et al. *Vasoactive intestinal peptide causes nitric oxide-dependent pulmonary vasodilation in isolated rat lung. Respiration* 64, 54-58. 1997; Saga, T. and Said, S. I. *Vasoactive intestinal peptide relaxes isolated strips of human bronchus, pulmonary artery, and lung parenchyma. Trans. Assoc. Am. Physicians.* 97, 304-310. 1984). Further studies show a high rate of VIP-R expression in the lung which is reflected in a high uptake of radiolabeled VIP in the lung of PPH patients who were injected 99mTc-VIP (e.g.: Raderer, M., Kurtaran, A., Hejna, M. et al. 123*I-labelled vasoactive intestinal peptide receptor scintigraphy in patients with colorectal cancer. Br. J. Cancer* 78, 1-5. 1998; Raderer, M, Kurtaran, A., Yang, Q. et al. *Iodine*-123-*vasoactive intestinal peptide receptor scanning in patients with pancreatic cancer. J. Nucl. Med.* 39, 1570-1575. 1998; Raderer, M., Kurtaran, A., Leimer, M. et al. *Value of peptide receptor scintigraphy using* (123)*I-vasoactive intestinal peptide and* (111)*In-DTPA-D-Phe*1-*octreotide in* 194 *carcinoid patients: Vienna University Experience,* 1993 *to* 1998. *J. Clin. Oncol.* 18, 1331-1336. 2000; Virgolini, I., Kurtaran, A., Raderer, M. et al. *Vasoactive intestinal peptide receptor scintigraphy. J. Nucl. Med.* 36, 1732-1739.1995).

Pituitary Adenylate Cyclase-Activating Polypeptide (PACAP):

PACAP is a neuropeptide isolated from the ovine hypothalamus consisting of the following 38 amino acid residues containing sequence (from N- to C-terminal):

```
                                         (SEQ ID No. 2)
His-Ser-Asp-Gly-Ile-Phe-Thr-Asp-Ser-Tyr-Ser-Arg-

Tyr-Arg-Lys-Gln-Met-Ala-Val-Lys-Lys-Tyr-Leu-Ala-

Ala-Val-Leu-Gly-Lys-Arg-Tyr-Lys-Gln-Arg-Val-Lys-

Asn-Lys.
```

Two forms of the peptide have been identified: PACAP-38 and the C-terminally truncated PACAP-27. PACAP-27 that shares 68 percent homology with VIP has the following sequence (from N- to C-terminal):

```
                                         (SEQ ID No. 3)
His-Ser-Asp-Gly-Ile-Phe-Thr-Asp-Ser-Tyr-Ser-Arg-

Tyr-Arg-Lys-Gln-Met-Ala-Val-Lys-Lys-Tyr-Leu-Ala-

Ala-Val-Leu
```

PACAP is very potent in stimulating adenylate cyclase and thus increasing adenosine 3,5-cyclic monophosphate (cAMP) in various cells. The compound functions as a hypothalamic hormone, neurotransmitter, neuromodulator, vasodilator, and neurotrophic factor. The major regulatory role of PACAP in pituitary cells appears to be the regulation of gene expression of pituitary hormones and/or regulatory proteins that control growth and differentiation of the pituitary glandular cells. These effects appear to be exhibited directly and indirectly through a paracrine or autocrine action. PACAP plays an important role in the endocrine system as a potent secretagogue for adrenaline from the adrenal medulla. The compound also stimulates the release of insulin. The stage-specific expression of PACAP in testicular germ cells during spermatogenesis suggests its regulatory role in the maturation of germ cells. In the ovary, PACAP is transiently expressed in the granulosa cells of the preovulatory follicles and appears to be involved in the LH-induced cellular events in the ovary, including prevention of follicular apoptosis. In the central nervous system, PACAP acts as a neurotransmitter or a neuromodulator. More important, PACAP is a neurotrophic factor that may play a significant role during the development of the brain. In the adult brain, PACAP appears to function as a neuroprotective factor that attenuates the neuronal damage resulting from various insults. PACAP is widely distributed in the brain and peripheral organs, notably in the endocrine pancreas, gonads, and respiratory and urogenital tracts. Two types of PACAP binding sites have been characterized. Type I binding sites exhibit a high affinity for PACAP (and a much lower affinity for VIP), whereas type II binding sites have similar affinity for PACAP and VIP. Molecular cloning of PACAP receptors has shown the existence of three distinct receptor subtypes. These are the PACAP-specific PAC1 receptor, which is coupled to several transduction systems, and the two PACAP/VIP-indifferent VPAC1 and VPAC2 receptors, which are primarily coupled to adenylyl cyclase. PAC1 receptors are particularly abundant in the brain and pituitary and adrenal glands whereas VPAC receptors are expressed mainly in the lung, liver, and testes.

SUMMARY OF THE INVENTION

The invention describes for the first time the clinical relevance of VIP, PACAP and compounds having the biological activity of VIP or PACAP for the treatment of sarcoidosis. VIP and PACAP are synthesized in various components of the central nervous system, e.g. specific brain regions like hippocampus and cortex as well as in the pituitary gland and peripheral ganglia VIP is furthermore secreted by immune cells and by some neoplastic cells (e.g. pancreatic cancer).

It is object of the present invention to provide novel use of known compounds as well as novel compounds, which are useful for the prevention and/or treatment of sarcoidosis and methods wherein said compounds are used.

Surprisingly it was found that peptides or polypeptides comprising the highly conservative decapeptide sequence Arg-Lys-Gln-Met-Ala-Val-Lys-Lys-Tyr-Leu (SEQ ID No. 4) show highly efficacy when administered to patients suffering from sarcoidosis symptoms and disorders. Compounds comprising this sequence and having totally 10-60, preferably 10-38, more preferably 10-28 or 10-23 amino acid residues have very similar or identical biological function as VIP or PACAP which also comprise said highly conservative sequence. It is another result of the present invention that VIP, PACAP and also its truncated forms, for example PACAP-27, are also highly active compounds for the prophylaxis and treatment of sarcoidosis by inhibition and/or regulation of cellular processes underlying the said diseases in humans.

Generally, it was found that VIP- and PACAP-like peptides and polypeptides can show the above-described therapeutic function and efficacy which have the following amino acid sequence:

$(A)_n$-Arg-Lys-Gln-Met-Ala-Val-Lys-Lys-Tyr-Leu-$(B)_m$ wherein A, B is any natural occurring amino acid residue, A and B are independently from each other; and n, m is an integer having values from 0-25; n and m being independently from each other. The value of m is preferably 4-18, more preferably 5-15, and most preferably 10-15.

Polypeptides or peptides, wherein $(A)_n$ (if n>2) comprises the tripeptide sequences His-Ser-Asp and/or Phe-Thr-Asp in N-terminal direction near by (1-10 amino acid residues) above-specified decapeptide sequence have an enhanced activity.

Thus polypeptides, wherein
$(A)_n$ (if n>2) has the meaning of $(X)_o$-Phe-Thr-Asp-$(Y)_p$ and $(X)_o$ (if o>2) has the meaning of $(X')_q$-His-Ser-Asp-$(X'')_r$
wherein X, Y, X', X" is any natural occurring amino acid residue; and o, p, is an integer having values from 0-11, and r, q is an integer having values from 0-4, show especially improved efficacy. Preferred values of o and p are 0-8, more preferably 1-5. Preferred values of r are 0-2.

Preferred examples falling under the generic formula are (SEQ ID No. 1, VIP)
His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn;

(SEQ ID No. 2, PACAP-38)
His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys (SEQ ID No. 3, PACAP-27)
His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu;

This invention discloses also compounds falling under the above-specified formula: $(A)_n$-Arg-Lys-Gln-Met-Ala-Val-Lys-Lys-Tyr-Leu-$(B)_m$
wherein A, B is any natural occurring amino acid residue, A and B are independently from each other, and n, m is an integer having values from 0-25, n and m being independently from each other, provided that VIP, PACAP and PACAP-27 (truncated PACAP) is excluded. Preferred examples of these novel polypeptides are:

(SEQ ID No. 4)
(i) Arg-Lys-Gln-Met-Ala-Val-Lys-Lys-Tyr-Leu;

(SEQ ID No. 5)
(ii) Phe-Thr-Asp-$X^1$-$X^2$-$X^3$-$X^4$-$X^5$-Arg-Lys-Gln-Met-Ala-Val-Lys-Lys-Tyr-Leu-Asn-Ser-Ile-Leu-Asn;

(SEQ ID No. 6)
(iii) Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn;

(SEQ ID No. 7)
(iv) Phe-Thr-Asp-Ser-Tyr-Ser-Arg-Tyr-Arg-Lys-Gln-Met-Ala-Val-Lys-Lys-Tyr-Leu;

(SEQ ID No. 8)
(v) His-Ser-Asp-$X^1$-$X^2$-Phe-Thr-Asp-$X^3$-$X^4$-$X^5$-$X^6$-$X^7$-Arg-Lys-Gln-Met-Ala-Val-Lys-Lys-Tyr-Leu;

(SEQ ID No. 9)
(vi) His-Ser-Asp-Ala-Val-Phe-Thr-Asp-Asn-Tyr-Thr-Arg-Leu-Arg-Lys-Gln-Met-Ala-Val-Lys-Lys-Tyr-Leu;

(SEQ ID No. 10)
(vi) His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu;

(SEQ ID No. 11)
(vii) His-Ser-Asp-$X^1$-$X^2$-Phe-Thr-Asp-$X^3$-$X^4$-$X^5$-$X^6$-$X^7$-Arg-Lys-Gln-Met-Ala-Val-Lys-Lys-Tyr-Leu-$X^8$-$X^9$-$X^{10}$-$X^{11}$(-$X^{12}$);

(SEQ ID No. 12)
(viii) His-Ser-Asp-$X^1$-$X^2$-Phe-Thr-Asp-$X^3$-$X^4$-$X^5$-$X^6$-$X^7$-Arg-Lys-Gln-Met-Ala-Val-Lys-Lys-Tyr-Leu-$X^8$-$X^9$-$X^{10}$-$X^{11}$-$X^{12}$-$X^{13}$-$X^{14}$-$X^{15}$-$X^{16}$-$X^{17}$-$X^{18}$-$X^{19}$-$X^{20}$-$X^{21}$-$X^{22}$;

wherein $X^1$-$X^{22}$ is any naturally occurring amino acid residue.

To sum up, it is an object of this invention to provide the following topic:

A use and a method for treatment of a disease or a disorder correlated directly or indirectly with sarcoidosis symptoms in human lung comprising administering to a patient a compound having the biological activity of vasoactive intestinal peptide (VIP) or pituitary adenylate cyclase-activating polypeptide (PACAP); preferably these compounds are peptides or polypeptides comprising the highly conservative sequence Arg-Lys-Gln-Met-Ala-Val-Lys-Lys-Tyr-Leu (SEQ ID No. 4), more preferably, they comprise additionally the sequences His-Ser-Asp (SEQ ID No. 14) and/or Phe-Thr-Asp (SEQ ID No. 13).

A corresponding use and method, wherein the pulmonary arterial pressure is reduced to more than 10%, preferably more than 20%, most preferably between 10 and 30%, after administration of said peptides and/or polypeptides.

A corresponding use and a method, wherein the diastolic blood pressure is reduced to 5-25%, preferably to 10-20%, and the systolic blood pressure is reduced to 10-30%, preferably to 10-25%, after administration of said compounds.

DETAILED DESCRIPTION

Suitable compounds which have the therapeutic effect according to the invention, are compounds which have the same, but also reduced or enhanced, biological activity of VIP or PACAP. Preferred compounds according to the invention have the same or an enhanced biological activity. All compounds falling under this group comprise the sequence Arg-Lys-Gln-Met-Ala-Val-Lys-Lys-Tyr-Leu (SEQ ID No. 4).

The invention includes also derivatives of the disclosed peptides and polypeptides having the same biological activity.

The term "same biological activity" means the biological, physiological or therapeutic activity or functionality compared with the relevant properties of said peptides and polypeptides, preferably VIP or PACAP.

The term "derivative" means a peptide compound which derives more or less direct from the corresponding peptide, such as VIP or PACAP as such, and is altered by some additions, deletions, mutations or modifications without altering the biological properties of the parent peptide. Suitable VIP derivatives are, for example, disclosed in WO 8905857, WO 9106565, EP 0663406 and WO 9729126 (Fmoc protected VIP). The term includes also conjugates of peptides and polypeptides according to the invention which consist of the parent peptide or polypeptide coupled to lipophilic entities, such as liposomes. VIP-liposome products are, for example, disclosed in WO 9527496 or WO 9735561, and have improved properties with respect to bioavailability and proteolytic degradation. Furthermore, the term includes also fragments, slightly modified fragments including truncated forms.

The term "analogue" means a compound which may have a different structure and composition compared with the polypeptides and peptides according to the invention, preferably VIP, however without having altered biological properties. VIP analogues may be natural or synthetic peptides but also non-peptides. Preferably, VIP analogues according to the invention are peptides. Examples for known VIP analogues are disclosed in EP 0325044 (cyclic peptides), EP 0225020 (linear peptides), EP 0536741 (cyclic VIP modifications), EP 0405242, EP 0184309 and EP 0613904. The term includes also VIP or PACAP homologues, which are not VIP or PACAP but show great structural similarity to VIP. Such a VIP homologue according to the invention is PACAP itself and its truncated form PACAP-27. The term also includes such homologues which could form, like VIP, amphipathic helices. Preferred VIP/PACAP homologues are peptides that comprise one or more consensus sequences. Examples are peptide histidine isoleucine (PHI), peptide histidine methionine (PHM), human growth hormone releasing factor (GRF), pituitary adenylate cyclase activating peptide (PACAP), secretin and glucagon.

The term "stabilized form" means a derivative or analogue wherein the parent peptide was altered in order get more stability and increased half-life in blood and serum. Such stabilized to forms are preferred if the polypeptide is rented by enzyme activity. Possible stabilized forms are cyclic peptides or polypeptides like cyclic VIP or Vyclic PACAP, fusion proteins, preferably Fc-fusion proteins or pegylated polypeptides, for example pegylated VIP or PACAP. Methods for manufacturing such polypeptides are well known in the art. Polypeptides and proteins may be protected against proteolysis by the attachment of chemical moieties. Such attachment may effectively block the proteolytic enzyme from physical contact with the protein backbone itself, and thus prevent degradation. Polyethylene glycol is one such chemical moiety which has been shown to protect against proteolysis (Sada, et al., J. Fermentation Bioengineering 71: 137-139, 1991). In addition to protection against proteolytic cleavage, chemical modification of biologically active proteins has been found to provide additional advantages under certain circumstances, such as increasing the stability and circulation time of the therapeutic protein and decreasing immunogenicity. (U.S. Pat. No. 4,179,337; Abuchowski et al., Enzymes as Drugs; J. S. Holcerberg and J. Roberts, eds. pp. 367-383, 1981; Francis, *Focus on Growth Factors* 3: 4-10; EP 0 401 384). The addition of polyethylene glycol increases stability of the peptides and polypeptides of this invention at physiological pH as compared to non-pegylated compounds. The pegylated polypeptide/protein is also stabilized with regard to salts.

The term "fusion protein" means a compound, especially a stabilized form, consisting of a polypeptide according to the invention, preferably VIP or a VIP derivative or analogue, such as PACAP, which is fused to another peptide or protein. Such a protein is preferably an immunoglobulin molecule, more preferably a fragment thereof, most preferably a Fc portion of an IgG molecule, preferably an IgG1. A Fc-VIP fusion protein shows an improved half-life in serum and blood. A further example is Fc-PACAP and FC PACAP-27.

The compound according to the invention can be used as medicament or as diagnostic means to evaluate pathological conditions in an individual.

The term "individual" preferably refers to mammals, especially humans. The compound is used in a pharmaceutical composition and formulations, comprising, as a rule, a pharmaceutically acceptable carrier, excipient or diluents. Techniques for the formulation and administration of the compounds of the present invention may be found in "Remington's Pharmaceutical Sciences" Mack Publishing Co., Easton Pa.

As used herein, the term "pharmaceutically acceptable carrier" means an inert, non toxic solid or liquid filler, diluent or encapsulating material, not reacting adversely with the active compound or with the patient, or any other formulation such as tablets, pills, dragees, capsules, gels, syrups, slurries, suspensions and the like. Suitable, preferably liquid carriers are well known in the art such as sterile water, saline, aqueous dextrose, sugar solutions, ethanol, glycols and oils, including those of petroleum, animal, vegetable, or synthetic origin, for example, peanut oil, soybean oil and mineral oil.

The formulations according to the invention may be administered as unit doses containing conventional non-toxic pharmaceutically acceptable carriers, diluents, adjuvants and vehicles which are typical for parenteral administration.

The term "parenteral" includes herein subcutaneous, intravenous, intra-articular and intratracheal injection and infusion techniques. Parenteral compositions and combinations are most preferably administered intravenously either in a bolus form or as a constant fusion according to known procedures.

Also other administrations such as oral administration or administration by inhalation or nasal spray are suitable.

Tablets and capsules for oral administration contain conventional excipients such as binding agents, fillers, diluents, tableting agents, lubricants, disintegrants, and wetting agents. The tablets may be coated according to methods well known in the art.

For inhalations the compound according to the invention is preferably brought in an aerosol form. Aerosols and techniques to make them are well known in the art. Aerosols applicable by inhalers containing a peptide or polypeptide of the invention, for example, VIP or PACAP are preferred if direct pulmonary symptoms have to be treated.

Unit doses according to the invention may contain daily required amounts of the compound according to the invention, or sub-multiples thereof to make up the desired dose. The optimum therapeutically acceptable dosage and dose rate for a given patient (mammals, including humans) depends on a variety of factors, such as the activity of the specific active material employed, the age, body weight, general health, sex, diet, time and route of administration, rate of clearance, enzyme activity, the object of the treatment, i.e., therapy or prophylaxis and the nature of the disease to be treated. Therefore, in compositions and combinations in a treated patient (in vivo) a pharmaceutical effective daily dose of the compound of this invention is between about 5 ng and 200 μg/kg body weight, preferably between 20 ng and 20 μg/kg body weight.

Surprisingly, it was found that the peptides and polypeptides as defined above and in the claims, above all VIP and PACAP, have beneficial effects in the treatment of sarcoidosis as demonstrated in the following example. These data show a dramatic improvement for the treatment of as yet not sufficiently treatable diseases. It is a benefit of this invention that all tested polypeptides comprising the highly conservative decapeptide sequence as depicted in above are efficacious.

Example 1

A patient with severe sarcoidosis stadium 3 and secondary pulmonary hypertension was under therapy with cortocosteroids, furosemid, oxygen and an anticoagulant. Right heart catheterization (Swan-Ganz, Baxter, Irvine, Calif., USA) was performed to measure mean pulmonary artery pressure (mPAP), cardiac output (CO), mean arterial pressure (MAP), pulmonary capillary wedge pressure (PCWP) mixed venous oxygen saturation ($SvO_2$%) and systemic arterial oxygen pressure ($PaO_2$%) for and after treatment with VIP inhalation (200 μg in 12 ml 0.9% NaCl per day, 4×3 ml per inhalation) for 12 weeks. FEV1 (forced expiratory volume in one second), FVC (forced vital capacity), TLC (total lung capacity), AaDO2 (arterial-alveolar oxygen difference) of sarcoidosis patient is measured according to standard methods for and after treatment with VIP (200 μg in 12 ml 0.9% NaCl per day) for 12 weeks. VIP was inhaled for 12 weeks via the Micro-Drop Master Jet (MPV, Truma, Germany) using a particle size of 3 μm to provide alveolar deposition of the substance.

Hemodynamic and lung function parameters of the sarcoidosis patient before and after the treatment with VIP for 12 weeks are summary in Table 2.

In the 6-minutes walk test, the patient improved from 210 meters before treatment to 350 meters after the treatment

TABLE 2

|  | before treatment | after treatment |
| --- | --- | --- |
| Age | 69 | 69 |
| sex | f | f |
| NYHA | IV | III |
| FVC | 1.4 | 1.3 |
| FEV1 | 1.2 | 1.1 |
| TLC | 2.3 | 2.7 |
| AaDO2 | 39.0 | 37.0 |
| mPAP | 55 | 32 |
| CO | 3.9 | 4.9 |
| PCWP | 10 | 10 |
| PVR | 923 | 359 |
| SaO2 | 83.2 | 88.0 |
| SvO2 | 49.4 | 53.0 |
| PaCO2 | 55.0 | 52.0 |
| PaO2 | 47.0 | 54.0 |
| 6-Min.WT | 210 | 350 |
| mPAP | 54.0 | 26.0 |
| mAP | 84.0 | 98.0 |
| PCWP | 6.0 | 7.0 |
| CI | 2.1 | 2.7 |
| PVR | 985.0 | 313.0 |

REFERENCES

1. Newman L S, Rose C S, Maier L A. Sarcoidosis. N Engl J Med 1997; 336:1224-34.
2. Chesnutt A N. Enigmas in sarcoidosis. West J Med 1995; 162:519-26.
3. Rakel R E, ed. Conn's Current therapy 1995: latest approved methods of treatment for the practicing physician. Philadelphia: Saunders, 1995:195-9.
4. Crystal R G, Bitterman P B, Rennard S I, Hance A J, Keogh B A. Interstitial lung diseases of unknown cause. Disorders characterized by chronic inflammation of the lower respiratory tract (first of two parts). N Engl J Med 1984; 310: 154-66.
5. Staton G W Jr, Ingram R H Jr. Chronic diffuse infiltrative lung disease. In: Dale D C, Federman D D, eds. Scientific American medicine. New York: Scientific American, 1997: 11-24.
6. Winterbauer R H, Hutchinson J F. Use of pulmonary function tests in the management of sarcoidosis. Chest 1980; 78:640-7.
7. Muther R S, McCarron D A, Bennett W M. Renal manifestations of sarcoidosis. Arch Intern Med 1981; 141:643-5.
8. DeRemee R A. Sarcoidosis. Mayo Clin Proc 1995; 70:177-81.
9. Sharma O P, Maheshwari A, Thaker K. Myocardial sarcoidosis. Chest 1993; 103:253-8.
10. Eklund A G. Sarcoidosis. In: Rakel R E, ed. Conn's Current therapy, 1997: latest approved methods of treatment for the practicing physician. Philadelphia: Saunders, 1997:229-31.

The invention claimed is:

1. A method for treatment of sarcoidosis in human lung or secondary pulmonary hypertension due to sarcoidosis comprising administering to a patient suffering from sarcoidosis in human lung or secondary pulmonary hypertension due to sarcoidosis, a peptide or a polypeptide consisting of amino acid sequence:

His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn (SEQ ID NO. 1).

2. The method according to claim 1, wherein said peptide or polypeptide is in a stabilized form.

3. The method according to claim 1, wherein said peptide or polypeptide is administered to the patient in an aerosol form by inhalation.

4. A method for treatment of sarcoidosis in human lung or secondary pulmonary hypertension due to sarcoidosis comprising administering to a patient suffering from sarcoidosis in human lung or secondary pulmonary hypertension due to sarcoidosis, a peptide or a polypeptide comprising the amino acid sequence Arg-Lys-Gln-Met-Ala-Val-Lys-Lys-Tyr-Leu (SEQ ID NO: 4).

5. A method for treatment of sarcoidosis in human lung or secondary pulmonary hypertension due to sarcoidosis comprising administering to a patient suffering from sarcoidosis in human lung or secondary pulmonary hypertension due to sarcoidosis, a peptide or a polypeptide consisting of the amino acid sequence: His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys (SEQ ID NO: 2) or His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu (SEQ ID NO: 3).

* * * * *